United States Patent
Farazi et al.

(10) Patent No.: US 7,702,391 B1
(45) Date of Patent: Apr. 20, 2010

(54) MONITORING SHORT TERM FLUCTUATIONS IN PR INTERVALS FOLLOWING PREMATURE VENTRICULAR CONTRACTIONS

(75) Inventors: Taraneh Ghaffari Farazi, San Jose, CA (US); Euljoon Park, Valencia, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1199 days.

(21) Appl. No.: 11/265,704

(22) Filed: Nov. 1, 2005

Related U.S. Application Data

(63) Continuation of application No. 11/061,008, filed on Feb. 17, 2005, now abandoned.

(51) Int. Cl.
*A61N 1/362* (2006.01)
*A61B 5/0452* (2006.01)

(52) U.S. Cl. ......................................................... 607/25

(58) Field of Classification Search ............. 607/17–18, 607/9, 25–26
See application file for complete search history.

(56) References Cited

U.S. PATENT DOCUMENTS

| | | | |
|---|---|---|---|
| 4,798,211 A | 1/1989 | Goor | |
| 4,877,035 A | 10/1989 | Bogen | |
| 5,042,497 A * | 8/1991 | Shapland | 600/509 |
| 5,203,326 A | 4/1993 | Collins | |
| 5,330,507 A | 7/1994 | Schwartz | |
| 5,733,312 A | 3/1998 | Schloss | |
| 6,058,328 A | 5/2000 | Levine | |
| 6,381,493 B1 | 4/2002 | Stadler et al. | 607/9 |
| 6,442,420 B1 | 8/2002 | Julu | |
| 6,487,442 B1 | 11/2002 | Wood | 600/515 |
| 6,609,023 B1 | 8/2003 | Fischell et al. | 600/515 |
| 6,922,585 B2 | 7/2005 | Zhou | |
| 7,079,887 B2 | 7/2006 | Burnes | |
| 7,181,277 B1 * | 2/2007 | Shelchuk et al. | 607/9 |
| 7,580,747 B1 * | 8/2009 | Farazi et al. | 607/25 |
| 2002/0065473 A1 | 5/2002 | Wang | |
| 2002/0188170 A1 | 12/2002 | Santamore | |
| 2003/0171782 A1 | 9/2003 | Florio | |

(Continued)

FOREIGN PATENT DOCUMENTS

WO WO 03/086187 A1 10/2003

(Continued)

OTHER PUBLICATIONS

Guzik, et al. "A Phenomenon of Heart-Rate Turbulence, It's Evaluation, and Prognostic Value" Cardiac Electrophysiology Review, 2002; 6:256-261.*

(Continued)

*Primary Examiner*—Carl H Layno
*Assistant Examiner*—Jessica Sarcione
(74) *Attorney, Agent, or Firm*—Steven M. Mitchell

(57) ABSTRACT

Implantable systems, and methods for use therein, perform at least one of a cardiac assessment and an autonomic assessment. Short-term fluctuations in PR intervals, that follow the premature contractions in the ventricles, are monitored. At least one of a cardiac assessment and an autonomic assessment is performed based on the monitored fluctuations in PR intervals that follow the premature contractions in the ventricles. This can include assessing a patient's risk of sudden cardiac death (SCD), assessing a patient's autonomic tone and/or detecting myocardial ischemic events based on the monitored fluctuations in PR intervals that follow the premature contractions in the ventricles.

28 Claims, 7 Drawing Sheets

U.S. PATENT DOCUMENTS

| | | | |
|---|---|---|---|
| 2003/0191403 A1 | 10/2003 | Zhou et al. | 600/515 |
| 2004/0122478 A1* | 6/2004 | Stadler et al. | 607/17 |
| 2004/0186525 A1 | 9/2004 | Burnes et al. | 607/17 |
| 2004/0215090 A1* | 10/2004 | Erkkila et al. | 600/515 |
| 2006/0094967 A1* | 5/2006 | Bennett et al. | 600/508 |

FOREIGN PATENT DOCUMENTS

| | | |
|---|---|---|
| WO | WO 03086187 A1 | 10/2003 |

OTHER PUBLICATIONS

Arnol, M. et al., "Atrioventricular Conduction Variability in Coronary Patients", Journal of Electrocardiology, vol. 36 No. 4, 2003, pp. 311-319.*

Aron, L. et al., "Prolonged PR interval associated with an abnormal frontal plane QRS axis as an electrocardiographic criterion of left ventricular function", International Journal of Cardiology, vol. 19, 1988, pp. 327-334.*

Haft, J. et al., "Effects of Ventricular Premature Contractions on Atrioventricular Conduction: Studies with His Bundle Electrography", The American Journal of Cardiology, vol. 32, Nov. 1973, pp. 794-798.*

Wichterle, D. et al., "Paradoxical Autonomic Modulation of Atrioventricular Nodal Conduction During Heart Rate Turbulence", PACE, vol. 26, Jan. 2003, Part II, pp. 440-443.*

Bauer, et al.; "Heart Rate Turbulence"; J Electrocardiol, 2003; 36 Suppl: 89-93.

Barthel, et al.; "Risk Stratification After Acute Myocardial Infarction by Heart Rate Turbulence"; Circulation, 2003; 108: 1221.

Mrowka, et al.; "Blunted Arterial Baroreflex Causes 'Pathological' Heart Rate Turbulence"; Am J Physiol Regul Integr Comp Physiol 279: R1171-R1175, 2000; 0363-6119/00.

Schmidt, et al.; "Heart Rate Turbulence After Ventricular Premature Beats as a Predictor of Mortality after Acute Myocardial Infarction"; Lancet. Apr. 24, 1999; 353(9162): 1390-1396.

Bonnemeier, et al.; "Reflex Cardiac Activity in Ischemia and Reperfusion: Heart Rate Turbulence in Patients Undergoing Direct Percutaneous Coronary Intervention for Acute Myocardial Infarction"; Circulation 2003; 108: 958-964.

Watanabe, et al.; "Effects of Ventricular Premature Stimulus Coupling Interval on Blood Pressure and Heart Rate Turbulence"; Circulation 2002; 106: 325-330.

Wichterle, et al.; "Mechanisms Involved in Heart Rate Turbulence"; Card Electrophysol Rev. Sep. 2002; 6(3) 262-266.

Schmidt et al. "Heart-Rate Turbulence after Ventricular Premature Beats as a Predictor for Mortality After Acute Myocardial Infarction", The Lancet, vol. 353, Apr. 24, 1999, pp. 1390-1396 (6 pages).

Bauer, "Heart-Rate Turbulence", J Electrocardiol. 2003, 36 Suppl: 89-93, 1 page.

Barthel et al., "Risk Stratification After Acute Myocardial Infarction b Heart Rate Turbulence", Circulation, 2003; 108:1221, 11 pages.

Mrowka et al., "Blunted Arterial Baroreflex Causes "Pathological" Heart Rate Turbulence", Am J Physiol Regulatory Integrative Comp Physiol 279: R1171-R1175, Issue 4, Oct. 2000, 9 pages.

Watanabe et al., "Effects of Ventricular Premature Stimulus Coupling Interval on Blood pressure and Heart Rate Turbulence", Circulation, 2002; 106:325-330.

Bonnemeier et al., "Reflex Cardiac Activity in Ischemia and Reperfusion Heart Rate Turbulence in Patients Undergoing Direct Percuatneous Coronary Intervention for Acute Myocardial Infarction", Circulation, 2003; 108:958-964.

Wichterle et al., "Mechanisms Involved in Heart Rate Turbulence", Cardiac Electrophysiology Review 2002, Sep.; 6(3) 262-266.

Guzik et al., A Phenomenon of Heart-Rate Turbulence, its Evaluation, and Prognostic Value', Card Electrophysiol Rev Sep. 2002; 6(3):256-61.

Lin et al., "A Phenomenology Model of Normal Sinus Rhythm in Healthy Humans", IEEE Trans Biomed Eng Feb. 2002; 49(2): 97-109.

Lin et al., "Tight Mechanism Correlation Between Heart Rate Turbulence and Baroreflex Sensitivity: Sequential Autonomic Blockade Analysis", J Cariovase Electrophysiol May 2002; 13(5): 427-31.

Malik et al., "Heart Rate Turbulence", G Ital Cariol, vol. 29, Suppl 5, 1999, 5 pages.

Berkowitsch et al., "Prognostic Significance of Heart-Rate Turbulence in ICD Patients with DCM", The XIIth world Congress on 102431, Publishing ID: 396, 1 page.

Cygankiewicz et al., "Heart Rate Turbulence Predicts Cardiac Death in Patients Undergoing CABG Surgery", Abstract ID: 102431, Publishing ID: 396, 1 page.

Bauer et al., "Dynamics of Heart Rate Turbulence Predicts Mortality After Acute Myocardial Infartion", 1 page.

Wichterle et al., "Turbulence Slope after Atrial premature Complexes is Significant Mortality Predictor in Patients after Myocardial Infarcation", Abstract: 814-4, Citation: Supplement to Journal of the American College of Cardiology, Mar. 19, 2003, vol. 41, Issue 6, Suppl. A, 2 pages.

Lindgren et al., "Heart Rate Turbulence after Ventricular and Atrial premature Beats in Subjects without Structural Heart Disease", Abstract, Journal of Cardiovascular Electrophysiology, vol. 14, Issue 5, p. 447, May 2003.

"Heart Rate Turbulence Calculation", Technische Universitat Munchen, 2 pages.

"Heart Rate Turbulence HRT!View", Technische Universitat Munchen, 2 pages.

Jeron et al., "Association of the Heart Rate Turbulence with Classic Risk Stratification Parameters in Postmyocardial Infarction Patients", A.N.E., Oct. 2003, vol. 8, No. 4, pp. 296-301.

Davies et al., "Relation of Heart Rate and Blood Pressure Turbulence Following Premature Ventricular Complexes to Baroreflex Sensitivity in Chronic Congestive Heart Failure", The American Journal of Cardiology, vol. 87, Mar. 15, 2001, pp. 737-742.

Schwab et al., "Influence of the point of origin on heart rate turbulence after stimulation ventricular and atrial premature beats", Bsic Res Cardiol., 2004, 99:56-60.

Vikman et al., "Heart Rate Turbulence after Atrial Premature Beats before Spontaneous Onset of Atrial Fibrillation" Journal of the American College of Cardiology, 2005; 45(2):278-284.

Non-Final Office Action mailed Mar. 27, 2007: Related U.S. Appl. No. 11/061,008.

Final Office Action mailed Sep. 28, 2007: Related U.S. Appl. No. 11/061,008.

Non-Final Office Action mailed Mar. 27, 2007: Related U.S. Appl. No. 11/061,008.

Non-Final Office Action mailed Oct. 4, 2005: Related U.S. Appl. No. 10/652,443.

Non-Final Office Action mailed Mar. 23, 2006: Related U.S. Appl. No. 10/652,443.

Final Office Action mailed Feb. 27, 2007: Related U.S. Appl. No. 10/652,443.

Non-Final Office Action mailed Feb. 26, 2008: Related U.S. Appl. No. 10/652,443.

Non-Final Office Action mailed Dec. 5, 2008: Related U.S. Appl. No. 10/652,443.

Non-Final Office Action mailed Jun. 10, 2009: Related U.S. Appl. No. 10/652,443.

Non-Final Office Action mailed Sep. 13, 2006: Related U.S. Appl. No. 10/861,747.

Non-Final Office Action mailed Mar. 28, 2007: Related U.S. Appl. No. 10/861,747.

Final Office Action mailed Oct. 17, 2007: Related U.S. Appl. No. 10/861,747.

Non-Final Office Action mailed Aug. 5, 2008: Related U.S. Appl. No. 11/181,719.

Final Office Action mailed Mar. 17, 2009: Related U.S. Appl. No. 11/181,719.

Notice of Allowance mailed Jun. 10, 2009: Related U.S. Appl. No. 11/181,719.

* cited by examiner

MONITORING SHORT TERM FLUCTUATIONS IN PR INTERVALS FOLLOWING PREMATURE VENTRICULAR CONTRACTIONS

PRIORITY CLAIM

The present application is a continuation-in-part (CIP) of U.S. patent application Ser. No. 11/061,008, entitled "Systems and Methods for Detecting Ischemic Events," filed Feb. 17, 2005 now abandoned.

CROSS REFERENCE TO RELATED APPLICATIONS

The present invention relates to the following commonly assigned applications, each of which is incorporated herein by reference: U.S. patent application Ser. No. 10/652,443, entitled "Implantable Cardiac Stimulation Device and Method that Measures Vagal Tone and Provides Responding Therapy," filed Aug. 28, 2003; U.S. patent application Ser. No. 10/861,747, entitled "System and Method for Using Vagal Stimulation to Assess Autonomic Tone and Risk of Sudden Cardiac Death in an Implantable Cardiac Device," filed Jun. 4, 2004; and U.S. patent application Ser. No. 11/181,719, entitled "Inducing Premature Atrial Contractions for the Purpose of Monitoring Autonomic Tone, Risk of Sudden Cardiac Death and Ischemic Events," filed Jul. 13, 2005, which issued as U.S. Pat. No. 7,580,747.

FIELD OF THE INVENTION

The present invention relates generally to implantable systems and methods for performing a cardiac assessment and/or an autonomic assessment, such as, assessing a patient's risk of sudden cardiac death, assessing a patient's autonomic tone, and detecting myocardial ischemic events.

BACKGROUND

A ventricular premature beat (VPB) triggers fluctuation in cardiac cycle duration and a brief disturbance to arterial blood pressure, referred to as heart rate turbulence (HRT) by Schmidt et al., "Heart-rate turbulence after ventricular premature beats as a predictor of mortality after acute myocardial infarction," *Lancet* 353:1390-96 (1999). Schmidt et al. define HRT as a characteristic initial acceleration and subsequent deceleration of sinus rhythm after a single VPB. The study by Schmidt et al. shows that the degree of HRT following a VPB can predict a patient's risk of SCD; for example, HRT is absent in the sinus rhythm of a high-risk patient but is present in the sinus rhythm of a low-risk patient. Schmidt et al. also defined two parameters to quantify the degree of HRT following a VPB: HRT onset, which is the initial acceleration of sinus rhythm after a single VPB, and HRT slope, which is the speed of the subsequent deceleration of sinus rhythm after a single VPB.

The degree of HRT following a VPB can also detect autonomic abnormalities. For example, U.S. Patent Application Publication No. 2003/0191403 A1, entitled "Method and apparatus for predicting recurring ventricular arrhythmias," to Zhou et al., explains that changes in the autonomic nervous system are known contributing factors to arrhythmia development. Zhou et al. further explain that heart rate is regulated by the sympathetic and parasympathetic components of the autonomic nervous system, and that increased sympathetic activity (i.e., sympathetic tone) causes the heart rate to increase, while increased parasympathetic activity (i.e., vagal tone) causes the heart rate to decrease. Accordingly, Zhou et al. propose that monitoring changes in autonomic tone might be useful for predicting arrhythmia development.

A study by Lin et al., "Tight mechanism correlation between heart rate turbulence and baroreflex sensitivity: sequential autonomic blockade analysis," *Journal of Cardiovascular Electrophysiology*, 13:427-431 (May 2002), demonstrated that because HRT is abolished when the vagus nerve is blocked, maintenance of normal HRT following a VPB is dependent on vagal tone. Lin et al. also showed that the parameters HRT onset and HRT slope are vagally dependent and, accordingly, can be used as indirect measures of vagal tone.

Additionally, Lin et al. showed that the parameters HRT onset and HRT slope are highly correlated with spontaneous baroreflex, which is described by Lin et al. as the negative feedback system that modulates dynamic fluctuations of heart rate and arterial blood pressure. A study by Mrowka et al., "Blunted arterial baroreflex causes 'pathological' heart rate turbulence," *Am J Physiol Regulatory Integrative Comp Physiol*, 279:R1171-75 (2000), explained that a VPB followed by a compensatory pause leads to a drop in arterial blood pressure; therefore, baroreflex action is essential for compensating blood pressure. Wichterle et al., "Mechanisms involved in heart rate turbulence," *Cardiac Electrophysiology Review*, 6:262-266 (2002) propose that the compensatory pause following a VPB triggers HRT as a response to the sudden decrease in arterial blood pressure.

Current measures of HRT, including turbulence onset (TO), turbulence slope (TS) and turbulence timing (TT), are each narrowly defined to be based on specific measures of RR intervals. For example, turbulence onset (TO) is defined as the difference between the mean of the first two sinus RR intervals after a ventricular premature beat (VPB) and the last two sinus RR intervals before the VPB, divided by the mean of the last two sinus RR intervals before the VPB. Turbulence slope (TS) is defined as the maximum positive slope of a regression line assessed over any five subsequent sinus-rhythm RR intervals within the first 20 sinus-rhythm intervals after a VPB. HRT timing (TT) is defined as the first beat number of a five-beat RR sequence having the maximum regression slope. It would be useful if other alternative types of measures can be used to assess a patient's risk autonomic tone and risk of SCD.

Myocardial ischemia, which involves oxygen starvation of the myocardium, can lead to myocardial infarction and/or the onset of malignant arrhythmias if the oxygen starvation is not alleviated. Although myocardial ischemia is sometimes associated with the symptom of angina pectoris (i.e., chest pain), the majority of episodes of myocardial ischemia are asymptomatic or "silent."

A wide range of therapies are known for the treatment of myocardial ischemia once it is detected, including surgical revascularization, neural stimulation and use of a variety of biologically active agents or compounds which can remove blood clots, reduce cardiac workload or improve cardiac circulation. However, accurate and rapid detection of myocardial ischemia is necessary in order to reduce the morbidity and mortality from this often silent but deadly condition. In other words, without knowledge of the condition, it cannot be treated. Accordingly, what are also needed are new and/or improved techniques and system for detecting myocardial ischemic events.

BRIEF SUMMARY OF THE INVENTION

Embodiments of the present invention relate to implantable systems, and methods for use therein, that can perform at least one of a cardiac assessment and an autonomic assessment. In accordance with embodiments of the present invention, short-term fluctuations in PR intervals that follow a premature contraction in the ventricles are monitored. At least one of a cardiac assessment and an autonomic assessment is performed based on the monitored fluctuations in PR intervals that follow the premature contraction in the ventricles. In accordance with an embodiment of the present invention, this includes assessing a patient's risk of sudden cardiac death (SCD) based on the monitored fluctuations in PR intervals that follow the premature contraction in the ventricles. In accordance with another embodiment, a patient's autonomic tone is assessed based on the monitored fluctuations in PR intervals that follow the premature contraction in the ventricles. In a further embodiment, a myocardial ischemic event is detected based on the monitored fluctuations in PR intervals that follow the premature contraction in the ventricles.

This description is not intended to be a complete description of, or limit the scope of, the invention. Other features, aspects, and objects of the invention can be obtained from a review of the specification, the figures, and the claims.

DETAILED DESCRIPTION OF THE INVENTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein.

Exemplary ICD

Figure 1:
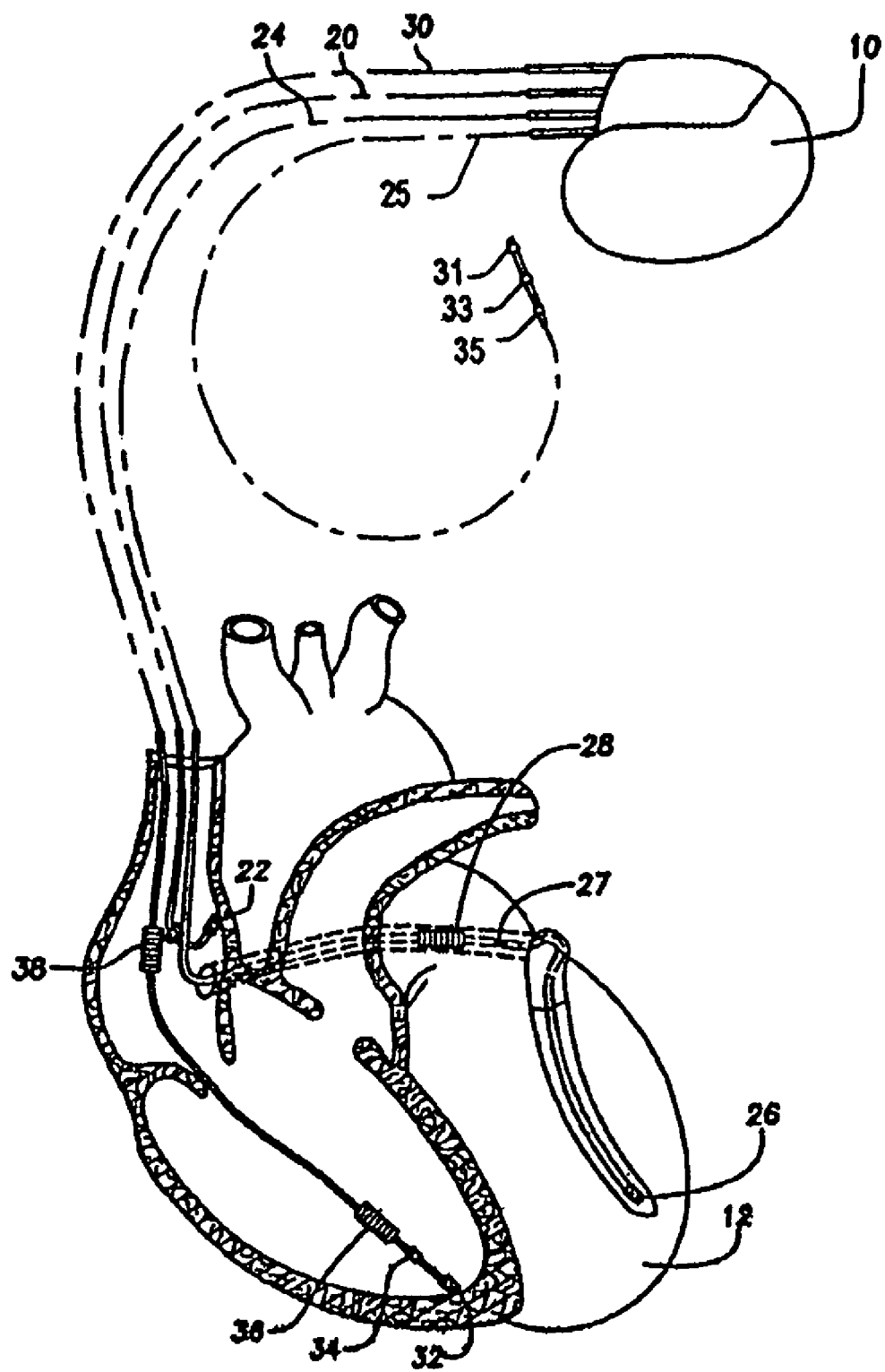
FIG. 1 is a simplified diagram illustrating an exemplary ICD in electrical communication with a patient's heart by means of three leads suitable for delivering multi-chamber stimulation and pacing therapy, and a fourth lead suitable for delivering vagal stimulation.
Figure 2:
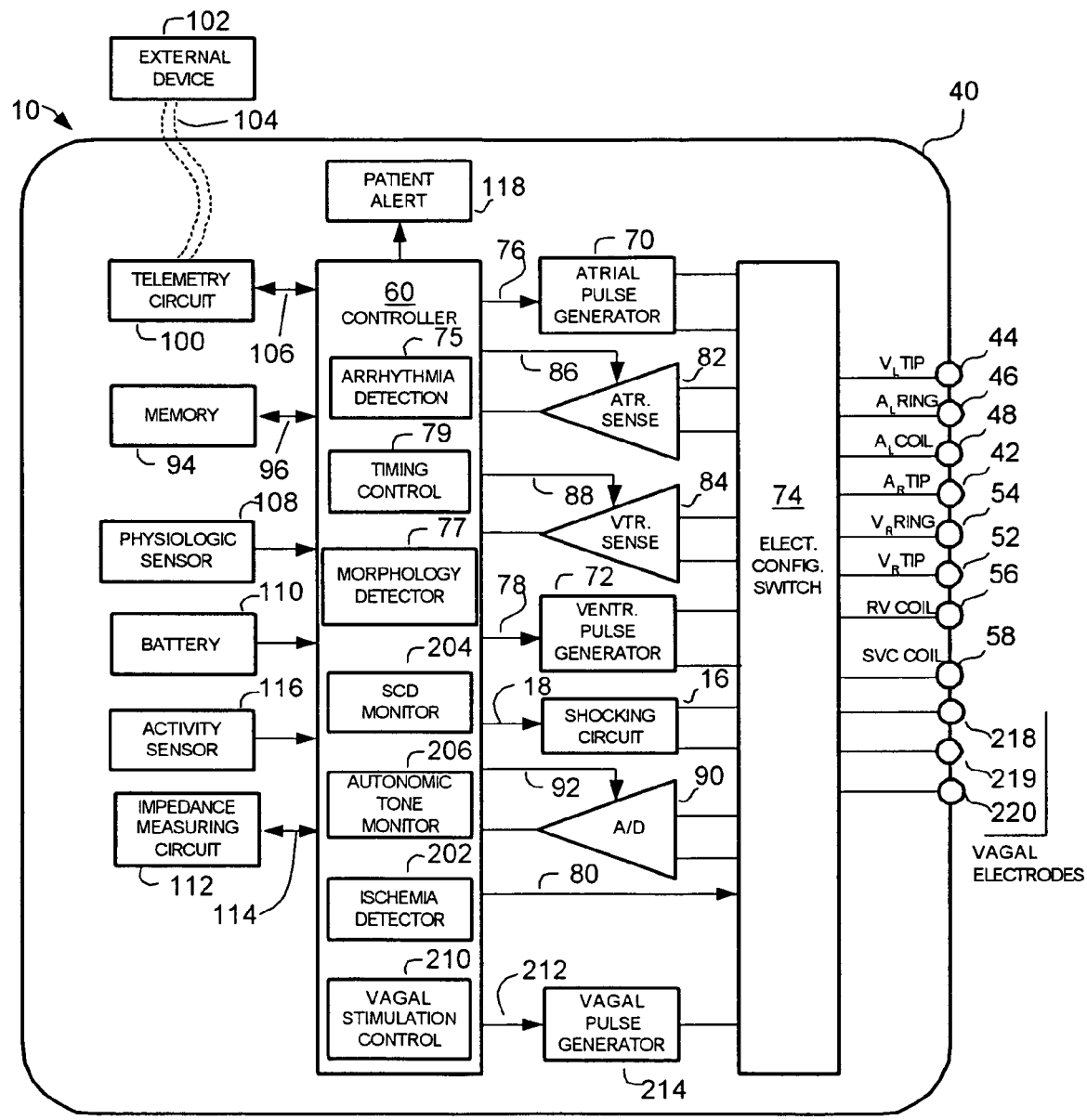
FIG. 2 is a functional block diagram of an exemplary ICD that can provide cardioversion, defibrillation, and pacing stimulation in four chambers of a heart, and assess a patient's risk of sudden cardiac death, assess a patient's autonomic tone and/or detect myocardial ischemic events, in accordance with embodiments of the present invention.

Before describing the invention in detail, it is helpful to describe an example environment in which the invention may be implemented. The present invention is particularly useful in the environment of an implantable cardiac device that can monitor electrical activity of a heart and deliver appropriate electrical therapy, for example, pacing pulses, cardioverting and defibrillator pulses, and drug therapy, as required. Implantable cardiac devices include, for example, pacemakers, cardioverters, defibrillators, implantable cardioverter defibrillators, and the like. The term "implantable cardiac device" or simply "ICD" is used herein to refer to any implantable cardiac device. FIGS. 1 and 2 illustrate such an environment in which embodiments of the present invention can be used.

Referring first to FIG. 1, an exemplary ICD 10 is shown in electrical communication with a patient's heart 12 by way of three leads, 20, 24 and 30, suitable for delivering multi-chamber stimulation and pacing therapy. To sense atrial cardiac signals and to provide right atrial chamber stimulation therapy, ICD 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, ICD 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

ICD 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the SVC. Accordingly, right ventricular lead 30 is capable of receiving cardiac signals and delivering stimulation in the form of pacing and shock therapy to the right ventricle.

In FIG. 1, ICD 10 is also shown as being in electrical communication with the patient's heart 12 by way of a vagal stimulation lead 25, having, e.g., three vagal stimulation electrodes 31, 33, and 35 capable of delivering stimulation bursts to the patient's vagus nerve. Alternatively, vagal stimulation electrodes 31, 33, and 35 can be positioned in the epicardial fat pad near the sinoatrial (SA) node. Based on the description herein, one skilled in the relevant art(s) will understand that the invention can be implemented by positioning vagal stimulation electrodes 31, 33, and 35 in alternate locations, such as in proximity to the cervical vagus, or implanted near or inside the SVC, the inferior vena cava (IVC), or the coronary sinus (CS), where they are also capable of delivering stimulation bursts to the patient's vagus nerve.

FIG. 2 shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 2, is often referred to as the "can," "case" or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, 58, 218, 219 and 220 (shown schematically and, for convenience, the names of the electrodes to which they are connected are shown next to many of the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

The connector is also shown as including vagal lead terminals (VAGAL ELECTRODES) 218, 219, and 220, which are configured for connection to vagal stimulation electrodes 31, 33, and 35, respectively, to support the delivery of vagal stimulation bursts.

At the core of ICD 10 is a programmable microcontroller 60, which controls the various modes of stimulation therapy. As is well known in the art, microcontroller 60 typically includes one or more microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the present invention. Rather, any suitable microcontroller 60 can be used to carry out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et. al.) and the state-machines of U.S. Pat. Nos. 4,712,555 (Sholder) and 4,944,298 (Sholder). For a more detailed description of the various timing intervals used within the ICD's and their interrelationship, see U.S. Pat. No. 4,788,980 (Mann et. al.). The '052, '555, '298 and '980 patents are incorporated herein by reference.

As shown in FIG. 2, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 76 and 78, respectively, to trigger or inhibit the stimulation pulses.

Also shown in FIG. 2, is a vagal pulse generator 214 that is controlled by vagal stimulation control 210 (within microcontroller 60) via a control signal 212, to trigger or inhibit the delivery of vagal stimulation pulses.

Microcontroller 60 further includes timing control circuitry 79, which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, a clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables ICD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 86.

For arrhythmia detection, ICD 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

More specifically, in accordance with an embodiment, microcontroller 60 utilizes arrhythmia detector 75 and morphology detector 77 to recognize and classify arrhythmia so that appropriate therapy can be delivered. The morphology detector 77 may also be used to detect signal morphologies that are useful for detecting ischemic events, in accordance with embodiments of the present invention described below. The arrhythmia detector 75 and morphology detector 77 can be implemented within the microcontroller 60, as shown in FIG. 2. Thus, these elements can be implemented by software, firmware, or combinations thereof. It is also possible that all, or portions, of these detectors can be implemented using hardware.

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via a control signal 92 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to heart 12 within each respective tier of therapy.

The operating parameters of ICD 10 may be non-invasively programmed into memory 94 through telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through established communication link 104.

For examples of such devices, see U.S. Pat. No. 4,809,697, entitled "Interactive Programming and Diagnostic System for use with Implantable Pacemaker" (Causey, III. et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

ICD 10 further includes a physiologic sensor 108 that can be used to detect changes in cardiac performance or changes in the physiological condition of the heart. Accordingly, microcontroller 60 can respond by adjusting the various pacing parameters (such as rate, AV Delay, RV-LV Delay, V-V Delay, etc.). Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream).

Also shown in FIG. 2 is an activity sensor 116. The activity sensor 116 (e.g., an accelerometer) can be used to determine the activity of the patient. Such information can be used for rate responsive pacing, or, in accordance with embodiments of the present invention, to determine whether the patient is sufficiently at rest such that certain baseline measurements can be obtained. If the sensor 116 is a multi-dimensional accelerometer, then posture information can also be extracted. The following patents, which are incorporated herein by reference, describe exemplary activity sensors that can be used to detect activity of a patient (some also detect posture): U.S. Pat. No. 6,658,292 to Kroll et al., entitled "Detection of Patient's Position and Activity Status using 3D Accelerometer-Based Position Sensor"; U.S. Pat. No. 6,466,821 to Kroll et al., entitled "Orientation of Patient's Position Sensor using External Field"; and U.S. Pat. No. 6,625,493 to Pianca et al., entitled "AC/DC Multi-Axis Accelerometer for Determining Patient Activity and Body Position." Simple activity sensors employ a piezoelectric crystal or a cantilever beam having a film of a piezoelectric polymer adhered to a surface of the beam. These are just a few exemplary types of activity sensors 116, which are not meant to be limiting.

The ICD 10 may also include a magnet detection circuitry (not shown), coupled to microcontroller 60. It is the purpose of the magnet detection circuitry to detect when a magnet is placed over ICD 10. A clinician may use the magnet to perform various test functions of ICD 10 and/or to signal microcontroller 60 that the external programmer 102 is in place to receive or transmit data to microcontroller 60 through telemetry circuit 100.

As further shown in FIG. 2, ICD 10 can have an impedance measuring circuit 112, which is enabled by microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to switch 74 so that any desired electrode may be used. The impedance measuring circuit 112 is not critical to the present invention and is shown only for completeness.

In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 16 by way of a control signal 18. The shocking circuit 16 generates shocking pulses of low (up to about 0.5 Joules), moderate (about 0.5-10 Joules), or high energy (about 11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognize), and pertaining exclusively to the treatment of fibrillation. Accordingly, microcontroller 60 is capable of controlling the synchronous or asynchronous delivery of the shocking pulses.

ICD 10 additionally includes a battery 110, which provides operating power to a load that includes all of the circuits shown in FIG. 2.

In accordance with an embodiment of the present invention, the controller 60 includes a sudden cardiac death (SCD) monitor 204, which as described in more detail below, can assess a patient's risk of SCD based on monitored short-term fluctuations in cardiac intervals (e.g., PR intervals) that follow premature contractions of the ventricles. The SCD monitor 204 can be implemented within the controller 60, as shown in FIG. 2. Thus, this monitor can be implemented by software, firmware, or combinations thereof. It is also possible that all, or portions, of the SCD monitor 204 can be implemented using hardware.

In accordance with an embodiment of the present invention, the controller 60 includes an autonomic tone monitor 206, which as described in more detail below, can assess a patient's autonomic tone based on monitored short-term fluctuations in cardiac intervals (e.g., PR intervals) that follow premature contractions of the ventricles. The autonomic tone monitor 206 can be implemented within the controller 60, as shown in FIG. 2. Thus, this monitor can be implemented by software, firmware, or combinations thereof. It is also possible that all, or portions, of the autonomic tone monitor 206 can be implemented using hardware.

In accordance with an embodiment of the present invention, microcontroller 60 includes an ischemia detector 202, which as described in more detail below, can detect ischemic events based on monitored short-term fluctuations in cardiac intervals (e.g., PR intervals) that follow premature contractions of the ventricles. The ischemia detector 202 can be implemented within the controller 60, as shown in FIG. 2. Thus, this detector can be implemented by software, firmware, or combinations thereof. It is also possible that all, or portions, of ischemia detector 202 can be implemented using hardware.

In accordance with specific embodiments, the SCD monitor 204, autonomic tone monitor 206 and/or ischemia detector 202 trigger the data acquisition circuit 90 and timing control circuit 79 to record cardiac intervals preceding and following premature contractions of the ventricles. The SCD monitor 204, autonomic tone monitor 206 and/or ischemia detector 202 measures, e.g., a degree of oscillatory behavior in the recorded cardiac intervals (e.g., PR intervals) in order to assess autonomic tone, and by monitoring changes in the degree of oscillatory behavior, can determine a patient's risk of SCD, a patient's autonomic tone and/or whether a patient is experiencing a myocardial ischemic event. Ischemia detector 202 can also trigger the ICD 10 to respond appropriately when a myocardial ischemic event is detected, as will be explained in more detail below. Similarly, the SCD monitor 204 and/or autonomic tone monitor 206 can trigger the ICD 10 to respond to specific assessments. Additionally, in conjunction with a telemetry circuit 100, the SCD monitor 204, autonomic tone monitor 206 and/or ischemia detector 202 can be configured to deliver status information, relating to the patient's risk of SCD, autonomic tone and/or ischemic events, to external device 102 through an established communication link 104. Ischemia detector 202 may also trigger a patient or physician alert in response to detecting a myocardial ischemic event. Similarly, SCD monitor 204 and/or autonomic tone monitor 206 may trigger an appropriate alert in response to assessing, e.g., a high risk of SCD and/or a specific autonomic tone. For example, a patient alert 118, which produces a vibratory or auditory alert, may be triggered.

While SCD monitor 204, autonomic tone monitor 206 and ischemia detector 202 are shown as separate blocks in FIG. 2, it is possible that such modules share software, firmware and/or hardware.

Assessing Risk of SCD

As mentioned above, it is known that a ventricular premature beat (VPB) triggers fluctuations in cardiac cycle duration and a brief disturbance to arterial blood pressure. Such fluctuations, which have been referred to as heart rate turbulence (HRT), have been shown to be a predictor of mortality after acute myocardial infarction. More specifically, it has been found that HRT is generally diminished or absent in the sinus rhythm of a patient at high-risk of SCD, but is more prominent or present in the sinus rhythm of a patient at low-risk. This will now be explained with reference to FIGS. 3A-3C.

Figure 3A:
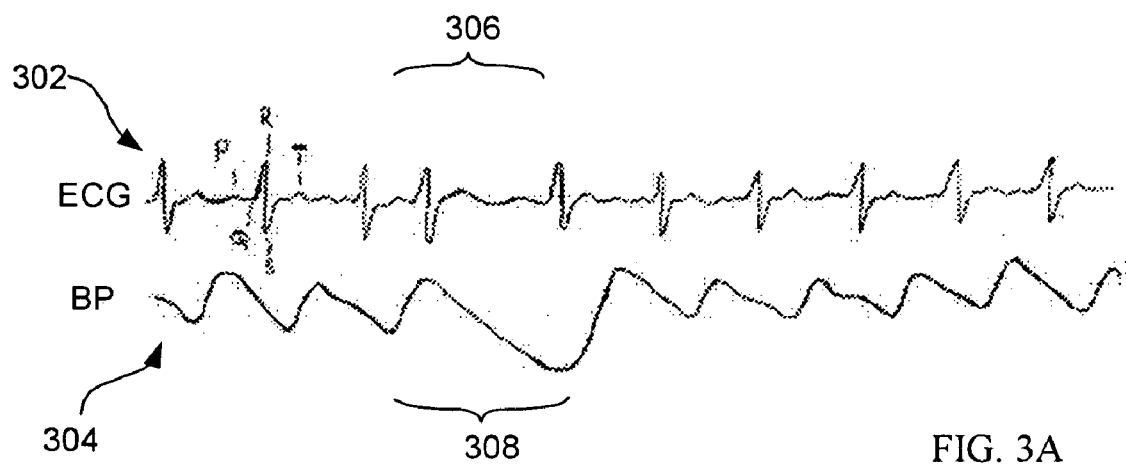
FIG. 3A illustrates an exemplary electrocardiogram (ECG) showing a premature contraction of the ventricles and a resulting disturbance in arterial blood pressure (BP).

FIG. 3A, which includes an exemplary ECG trace 302 and a blood pressure trace 304, can be used to show how a premature contraction in the ventricles causes a brief disturbance to arterial blood pressure. As can be appreciated from FIG. 3A, each cycle of the ECG waveform 302, which corresponds to a heart beat, includes a P wave that is a normally small positive wave caused by the beginning of a heart beat. Following the P wave there is a portion which is substantially constant in amplitude. The QRS complex of the ECG then normally occurs after the substantially constant portion, beginning with a Q wave that is normally a small negative deflection, which is then immediately succeeded by the R wave that is a rapid positive deflection. Following the R wave, the QRS complex is completed with an S wave that is generally characterized by a small positive inflection in the ECG signal. Following the S wave is a T wave, which is separated from the S wave by the ST segment. Various types of cardiac intervals (period of time between any two designated cardiac events) can be measured from an ECG signal. For example: an RR interval is the interval between successive R waves; a PP interval is the interval between successive P waves; a PR interval is the interval between a P wave and an R wave within the same beat; a QT interval is the interval between a Q wave and a T wave within the same beat; and an RT interval is the interval between an R wave and a T wave within the same beat. These are just a few examples of cardiac intervals that can be measured.

Still referring to FIG. 3A, a premature contraction in the ventricles is shown at 306 within the exemplary ECG trace 302. Also shown is an exemplary resulting disturbance 308 in the arterial blood pressure trace 304.

Figure 3B:
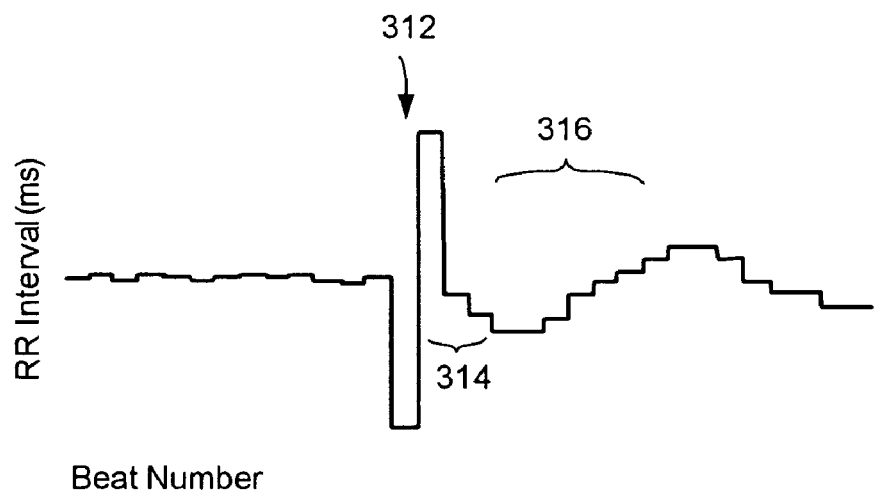
FIG. 3B illustrates the resulting fluctuation in sinus cycle lengths in response to a premature contraction of the ventricles for a patient not at high risk of sudden cardiac death (SCD).
Figure 3C:
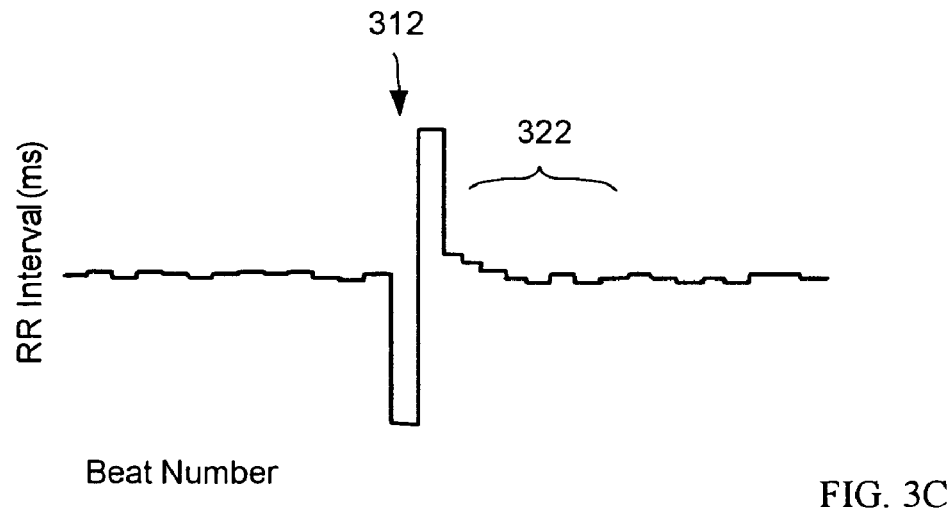
FIG. 3C illustrates the resulting fluctuation in sinus cycle lengths in response to a premature contraction of the ventricles for a patient at high risk of SCD.

FIGS. 3B and 3C are graphs of successive cardiac beats (horizontal axis) versus RR intervals (vertical axis), which are useful for monitoring the short-term fluctuation in RR intervals following a premature contraction of the ventricles. More specifically, FIG. 3B illustrates the resulting short-term fluctuation in sinus cycle lengths (i.e., RR intervals) following the premature contraction in the ventricles, for a patient with a low risk of SCD. In contrast, the resulting fluctuation in cardiac intervals (RR intervals, in this example) following a premature contraction in the ventricles, for a patient at high risk of SCD, is shown in FIG. 3C. As can be seen in both FIGS. 3B and 3C, a premature contraction in the ventricles can be recognized by the compensatory pause 312 in sinus cycle length. Following this pause 312, there is a pronounced and recognizable fluctuation in RR intervals in response to the premature contraction, when the patient is at a low risk of SCD, as shown in FIG. 3B. This pronounced fluctuation includes both an initial acceleration 314 and a subsequent deceleration 316 following the premature contraction. In contrast, when a patient is at high risk of SCD, there is a negligible fluctuation 322 in RR intervals in response to a premature contraction of the ventricles, as shown in FIG. 3C. This negligible fluctuation 322 can also be referred to as a blunted response. Using the terminology of Schmidt et al, the degree of HRT is much greater when a patient is at low risk for SCD, in comparison to when the patient is at high risk for SCD.

Accordingly, one approach for assessing a patient's risk of SCD is to measure the degree of HRT after a naturally occurring (i.e., intrinsic) premature ventricular contraction (PVC) caused by a VPB. It is also possible to asses a patient's risk of SCD by measuring the degree or HRT after a premature contraction of the ventricles is caused be an intrinsic premature atrial contraction (PAC), which conducts through the AV node and into the ventricles, thereby causing the ventricles to prematurely contract. A disadvantage of these techniques, however, is that they cannot be executed on-demand or at regular intervals.

Another approach for assessing a patient's risk of SCD, when naturally occurring premature contractions of the ventricles are absent, is to measure the degree of HRT following artificially induced premature contractions of the ventricles. Referring back to FIG. 2, this can be accomplished, e.g., by applying a single premature stimulus to the one of the ventricles using the ventricular pulse generator 72. A disadvantage of this technique, however, is that artificially inducing PVCs can cause an arrhythmia.

It is also possible that premature contractions in the ventricles can be caused, on demand, by inducing premature atrial contractions (PACs). In such an approach, the patient's right or left atrium is stimulated prematurely to artificially induce a PAC. Referring back to FIG. 2, this can be accomplished by applying a single premature stimulus to the atrium using the pulse generator 70. The induced PAC conducts through the AV node and into the ventricles, thereby causing the ventricles to prematurely contract, which results in a corresponding drop in blood pressure. An advantage of this technique is that it can be executed on-demand and at regular intervals, and is not likely to cause an arrhythmia.

An arterial blood pressure disturbance similar to that shown at 308 (FIG. 3A) can also be triggered by stimulating a patient's vagus nerve, as was disclosed in commonly invented and assigned U.S. patent application Ser. No. 10/861,747, which was incorporated herein by reference above. As explained in the '747 application, a short burst of stimulation to the vagus nerve induces a drop in atrial pressure, which simulates a patient's cardiovascular response to a premature contraction of the ventricles. Accordingly, such stimulation of the vagus nerve will often be referred to hereafter as "simulating" a premature contraction of the ventricles. This is accomplished by delivering, on demand, a short burst of stimulation to the vagus nerve to thereby induces a drop in atrial pressure, which simulates a patient's cardiovascular response to a premature contraction of the ventricles. More specifically, the patient's vagus nerve is stimulated for a duration that simulates compensatory pause 312 (FIG. 3B), in order to trigger an intrinsic baroreflex response to a drop in blood pressure. Referring back to FIG. 1, the vagal stimulation lead 25 can be used to deliver such stimulation. Referring back to FIG. 1, the vagal pulse generator 214 can produce the stimulation pulses delivered by the lead 25.

When the cardiac intervals being monitored are RR intervals, as shown in FIGS. 3B and 3C, turbulence onset (TO) quantifies the amount of initial acceleration 314. Schmidt et al. specifically define TO as the difference between the mean of the first two sinus RR intervals after a ventricular premature beat (VPB) and the last two sinus RR intervals before the VPB, divided by the mean of the last two sinus RR intervals before the VPB (thus, a measurement of TO is expressed as a percentage). It is however noted that one of ordinary skill in the art would understand the similar results can be obtained even if the definition of TO were slightly modified. For example, more than just the last two and first two RR intervals before and after a VPB can be considered (e.g., using the last three and first three RR intervals before and after a VPB may produce similar results). Accordingly, the term TO should not be limited to the strict definition provided by Schmidt et al., but rather, should also encompass equivalent measures.

When the cardiac intervals being monitored are RR intervals, as in FIGS. 3B and 3C, turbulence slope (TS) quantifies the speed of subsequent deceleration 316. Schmidt et al. specifically define TS as the maximum positive slope of a regression line assessed over any five subsequent sinus-rhythm RR intervals within the first 20 sinus-rhythm intervals after a VPB (thus, a measurement of TS is expressed in ms per RR interval). It is however noted that one of ordinary skill in the art would understand that similar results can be obtained even if the definition of TS were slightly varied. Similar results may be produced, e.g., if the regression line were assessed over any N subsequent sinus-rhythm RR intervals within the first M sinus-rhythm intervals after a VPB, where N and M need not be exactly 5 and 20, respectively. Accordingly, the term TS should not be limited to the strict definition provided by Schmidt et al., but rather, should also encompass equivalent measures.

As mentioned above, Watanabe et al. define HRT timing (TT) as the first beat number of a five-beat RR sequence having the maximum regression slope. It is however noted that one of ordinary skill in the art would understand that similar results can be obtained even if the definition of TT were slightly varied. For example, similar results may be obtained using the first beat number of an N-beat RR sequence having the maximum regression slope, where N need not be exactly 5.

It is believed that the blunting of short-term fluctuations in cardiac intervals that follow a premature contraction of the ventricles is primarily a vagally mediated phenomenon. Since the vagal nerve feeds the SA node as well as the AV node, in addition to affecting RR intervals, the inventors of the present invention believe that PR intervals that follow premature contractions of the ventricles will also be affected. Accordingly, in accordance with embodiments of the present invention, rather than (or in addition to) monitoring RR intervals, PR intervals are monitored for the purpose of monitoring short-term fluctuations in PR intervals that follow a premature contraction of the ventricles. In other words, PR intervals can be the cardiac intervals that are monitored for the purpose of determining whether a patient is at risk of SCD. As with RR intervals, PR intervals that both precede and follow a premature contraction can be monitored, such that PR intervals that precede the premature ventricular event can be used in calculating the short-fluctuations in PR intervals that follow the premature contraction of the ventricles.

These are just two examples of how cardiac intervals can be monitored. However, the present invention need not be limited to using only RR intervals and/or PR intervals. This is because it is believed that short-term fluctuations in these other types of cardiac intervals will also be blunted, following premature contractions. For example, short-term fluctuations in other types of cardiac intervals can be monitored, including, but are not limited to, PP, QT and RT intervals. However, it is noted that a graph of PR intervals, PP intervals, QT intervals or RT intervals versus beat number may not resemble to the graphs shown in FIGS. 3B and 3C discussed above (which show RR intervals versus beat number). Accordingly, it should be understood that the blunting of short-term fluctuations of these other cardiac intervals may not be detected using identical algorithms. Nevertheless, based on the description herein, one of ordinary skill in the art will be able define detection algorithms that appropriately take into account the specific cardiac interval or intervals being monitored.

Figure 4:
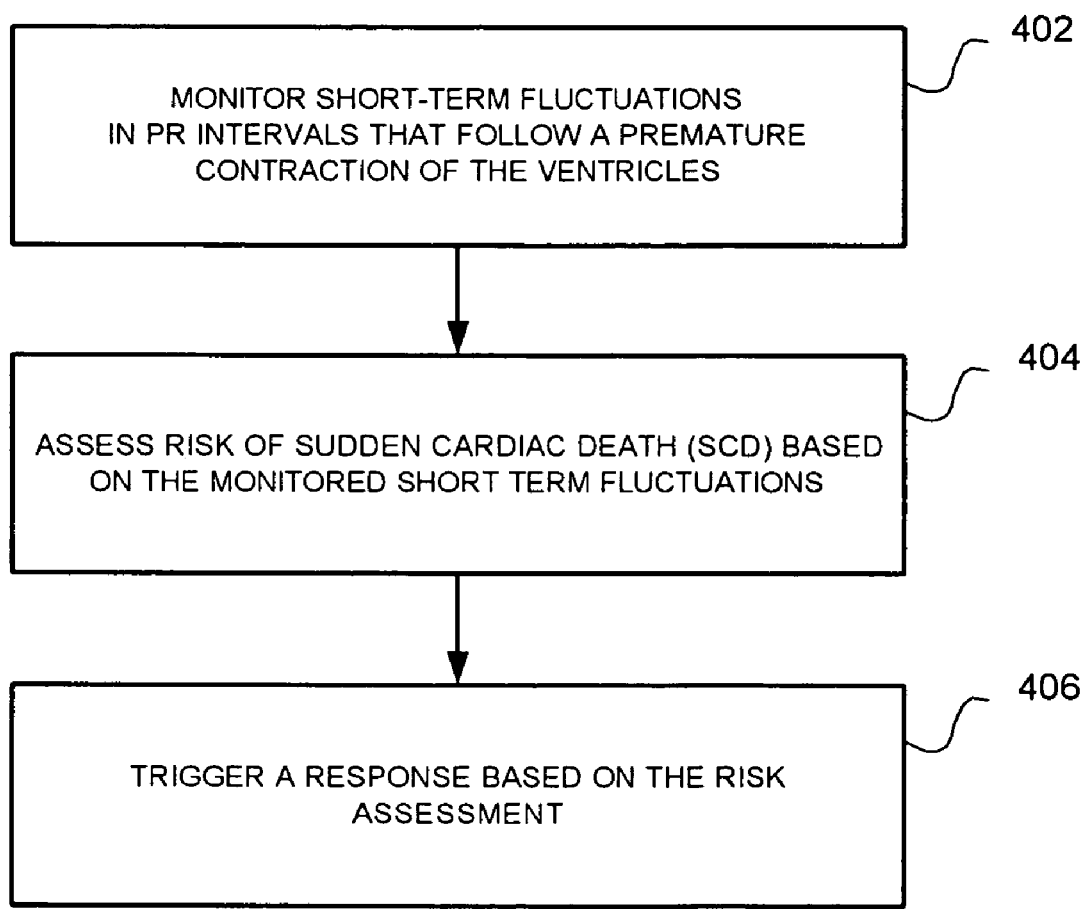
FIG. 4 is a high-level flow diagram that is useful for describing embodiments of the present invention that relate to assessing a patient's risk of SCD.

The flow diagram of FIG. 4 will now be used to describe how short-term fluctuations in PR intervals that follow a premature contraction in the ventricles can be monitored to assess a patient's risk of SCD. Such premature contractions of the ventricles can be intrinsic, induced by delivering stimulation to a ventricle, caused by inducing a premature atrial contraction, simulated by stimulating the vagus nerve, or combinations thereof.

Step 402 involves monitoring short-term fluctuations in PR intervals that follow a premature contraction of the ventricles. Any fluctuations (or lack thereof) in PR intervals that occur following a premature contraction of the ventricles will typically be recognizable only during the first 25 beats following the contraction. Thus, the phrase short-term, as used herein, generally refers to about the first 25 successive beats following a premature contraction of the ventricles, but can refer to even less than the first 25 successive beats (e.g., it can refer to as little as about the first 10 successive beats following a premature contraction of the ventricles). In other words, in accordance with an embodiment of the present invention, step 402 can be performed by monitoring fluctuations in PR intervals corresponding to the first N successive beats that follow a premature contraction of the ventricles, where N is an integer between 10 and 25. However, it is possible that N be another number, and/or that the PR intervals corresponding to some beats be excluded. It is also noted that step 404 may include monitoring PR intervals that both precede and follow a premature contraction, such that PR intervals that precede a premature contraction of the ventricles can be used in calculating the short-fluctuations in PR intervals that follow the premature contraction. That is, PR intervals corresponding to beats that occur prior to a premature contraction may also be monitored at step 402. This is discussed in more detail below.

At step 404, a risk of sudden cardiac death (SCD) is assessed based on the monitored fluctuations. Additional details of step 404 are also discussed below. Then, at step 406, one or more response can be triggered in response to the risk assessment. Many of these responses are discussed in more detail below.

In accordance with a specific embodiment of the present invention, at step 402, a number of PR intervals following a premature contraction of the ventricles (and possible a number of PR intervals preceding the premature contraction) are recorded for processing. In accordance with certain embodiments, step 402 includes quantifying the short-term fluctuations, and more specifically quantifying a degree of the short-term fluctuations in PR intervals that follow a premature contraction of the ventricles.

In specific embodiments, step 402 includes measuring one or more degree of heart rate turbulence (HRT), but substituting measures of PR intervals for measures of RR intervals that are typically used to measure degrees of HRT. Then, step 406 can include assessing risk of SCD based on the one or more measured degree of HRT. In such embodiments, step 406 may include comparing one or more degree of HRT to one or more corresponding threshold(s) and assessing the risk of SCD based on such comparisons.

Since each HRT parameter is expressed in different units, if more than one HRT parameter is being monitored, then a degree of HRT can be calculated using an algorithm that appropriately weights the different types of parameters to produce a single value. One or more appropriate threshold can be determined in a similar manner. Alternatively, a multi-dimensional table (e.g., a truth table) can be used such that each different type of parameter has its own corresponding threshold(s). A risk of SCD can then be assessed as desired. For example, it may be that a high risk of SCD is only assessed when every measured HRT parameter crosses a corresponding threshold (in a direction indicative of a diminished degree of HRT, or more generally, in a direction indicative of a diminished degree of short term fluctuations in cardiac intervals following a premature contraction of the ventricles). For another example, it may be that a high risk of SCD is identified when at least one HRT parameter is less than its corresponding threshold (indicating a diminished HRT).

Risk of SCD can be classified simply as high and low. Alternatively, there can be more than two levels of risk (e.g., there may also be a medium risk). Where there are more than two levels of risk of SCD, then multiple thresholds can be used to define the various risks, as would be appreciated by one of ordinary skill in the art. It is also possible to track the progression of risk of SCD by comparing a previously determined risk to a more recently determined risk, to thereby determine whether a risk of SCD has increased or decreased over a period of time. Additionally, a previously determined risk of SCD can be compared to a more recently determined risk for the purpose of determining whether there is an imminent risk of an arrhythmia. This can be accomplished, for example, by defining an imminent risk threshold that is based on previously determined assessments. For a more specific example, if it is determined that a risk of SCD has increased by a certain percentage (e.g., doubled) in less than a certain period of time (e.g., 24 hours), then a specific response can be triggered, indicating that there is an imminent risk of an arrhythmia. Exemplary responses are discussed below.

As mentioned above, step 402 is performed by monitoring short-term fluctuations in PR intervals that follow a premature contraction of the ventricles. However, it is noted that this may include monitoring PR intervals that both precede and follow a premature contraction, such that PR intervals that precede the premature event can be used in calculating the short-term fluctuations in PR intervals that follow the premature event. This can be accomplished in a similar manner as was described above where intervals that precede and follow a premature contraction of the ventricles are used to calculate turbulence onset (TO).

It is clear from the above description that the present invention can be implemented by measuring any one of a number of different parameters that quantify the oscillatory behavior of PR intervals following a premature contraction of the ventricles that also serve as surrogate measures of the level of vagal reflex activity. More generally, embodiments of the present invention are useful for assessing risk of SCD based on the short-term fluctuations in PR intervals that follow a premature contraction of the ventricles. This can be accomplished in any of the manners discussed above. It is also possible to monitor the overall morphology of the oscillations of PR intervals following a premature contraction of the ventricles. This can include comparing a monitored morphology to a threshold morphology, and assessing a risk of SCD based on the comparison. A monitored morphology can also be compared to previously monitored morphologies to detect changes (e.g., increases or decreases) in a risk of SCD.

If short-term fluctuations in more than one type of parameter following a premature contraction of the ventricles are being monitored, then a degree of fluctuations can be calculated using an algorithm that appropriately weights the fluctuations corresponding to the different types of parameters to produce a single value. An appropriate threshold can be determined in a similar manner. Alternatively, a multi-dimensional table (e.g., a truth table), or the like, can be used such that each different type of parameter has its own corresponding threshold. The assessment of risk of SCD can then be defined as desired. For example, it may be that a high risk of SCD is only assessed when all monitored parameters of short-term fluctuations cross corresponding thresholds (in a direction indicative of a diminished degree of HRT, or more generally, in a direction indicative of a diminished degree of short term fluctuations in cardiac intervals following a premature contraction of the ventricles). For another example, it may be that a high risk of SCD is assessed when at least one monitored parameter crosses a corresponding threshold (in a direction indicative of a diminished degree of HRT). More generally, it may be that a high risk of SCD is identified when n out of m monitored parameters are cross corresponding thresholds (in a direction indicative of a diminished degree of HRT). Measures of morphology can also be used in combinations with other types of measurements. These are just a few examples of how measurements of different types of parameters can be used to assess a risk of SCD. One of ordinary skill in the art would appreciate from this description that other ways are also within the spirit and scope of the present invention.

As mentioned above, at step 406 one or more response can be triggered based on the assessed risk of SCD. In accordance with an embodiment of the present invention, information related to a risk of SCD can be stored for later retrieval and/or transmission to a physician or other clinician. This can include, for example, storing the PR intervals, a degree of fluctuations in the PR intervals and/or a degree of risk of SCD. Such information can basically be displayed with previously determined risks of SCD, from say a month ago, and compared to see improvement or worsening of the risk of SCD. Such information can be continually, or from time to time, automatically uploaded to an external device (e.g., 102). Such an external monitoring device can be located, e.g., in the patients' home, and the information can be transmitted (e.g., through telephone lines or the Internet) to a medical facility where a physician can analyze the information. Alternatively, the external device can be located at a medical facility, and the information can be uploaded when the patient visits the facility.

In an embodiment, a patient is alerted when a risk of SCD is sufficiently high, to warrant an alert warning of impending arrhythmia, thereby allowing the patient to respond appropriately. Such an alert could be a vibratory or auditory alert that originates from within an implantable device. Alternatively, an implantable device may wirelessly transmit an alert to an external device that produces a visual or auditory alert that a patient can see or hear. The alert may inform that patient that he should rest, or if the patient is operating some type of dangerous machinery (e.g., a car), that the patient should stop what they are doing. By alerting the patient to rest, a myocardial infarction may be avoided, or if it does occur, the patient will be less dangerous to themselves and others if the patient is resting when the infarction or VTNF occurs (as opposed, e.g., to driving a car).

Additionally or alternatively, the patient can be instructed to take medication when alerted. In still another embodiment, a physician or other person (e.g., a caregiver, guardian or relative of the patient) is alerted whenever a high risk of SCD is assessed.

In further embodiments, a therapy can be triggered in response to assessing a high risk of SCD. One type of therapy would be for an implanted device (e.g., device 10) to stimulate the vagal nerve, in an attempt to slow down the heart rate.

In another embodiment, the implanted device, if appropriately equipped, can deliver an appropriate drug therapy. One of ordinary skill in the art would appreciate from the above description that other types of therapies can be triggered.

These are just a few examples of the types of responses that can be performed upon assessing a high risk of SCD. One of ordinary skill in the art would understand from the above description that other responses are also possible, while still being within the spirit and scope of the present invention.

Fluctuations in PR intervals may be normally attenuated (i.e., blunted) at higher heart rates. Accordingly, it may be beneficial to also monitor heart rate and or activity (using a single or multi-dimensional activity sensor) and to store such information together with the information used to assess the risk of SCD and/or information relating to an assessed risk of SCD.

Steps 402 and 404 can be repeated from time to time so that changes in a patient's risk of SCD can be monitored. It is also within the scope of the present invention that step 402 is repeated multiple times (e.g., 20 times) before a risk of SCD is assessed at step 404. For example, a total of 20 premature contractions of the ventricles may be detected, induced or simulated, with each premature contraction of the ventricles being separated by, e.g., 20 normal sinus ventricular contractions. A separate risk of SCD can be then be assessed following each premature contraction of the ventricles, and then a combined risk can be determined. Alternatively, cardiac interval data associated with all 20 premature ventricular contractions can be ensemble averaged, and a risk of SCD can be assessed based on the ensemble averages. These are just a few examples of how fluctuations in PR intervals that follow premature contractions of the ventricles can be used to monitor a patient's risk of SCD. Based on the description herein, those of ordinary skill in the art will appreciate that other ways are also within the spirit and scope of the present invention.

Monitoring Autonomic Tone

In addition to being indicative of a risk of SCD, measures of autonomic tone could be used to provide an indication of the progression of a disease state, such as heart failure. For example, an increase in sympathetic tone (and a decrease in parasympathetic tone) is indicative of a worsening heart failure condition. Conversely, a decrease in sympathetic tone (and an increase in parasympathetic tone) is indicative of an improving heart failure condition. Accordingly, embodiments of the present invention can be more generally used to assess a patient's autonomic tone, as briefly described with reference to FIG. 5.

Figure 5:
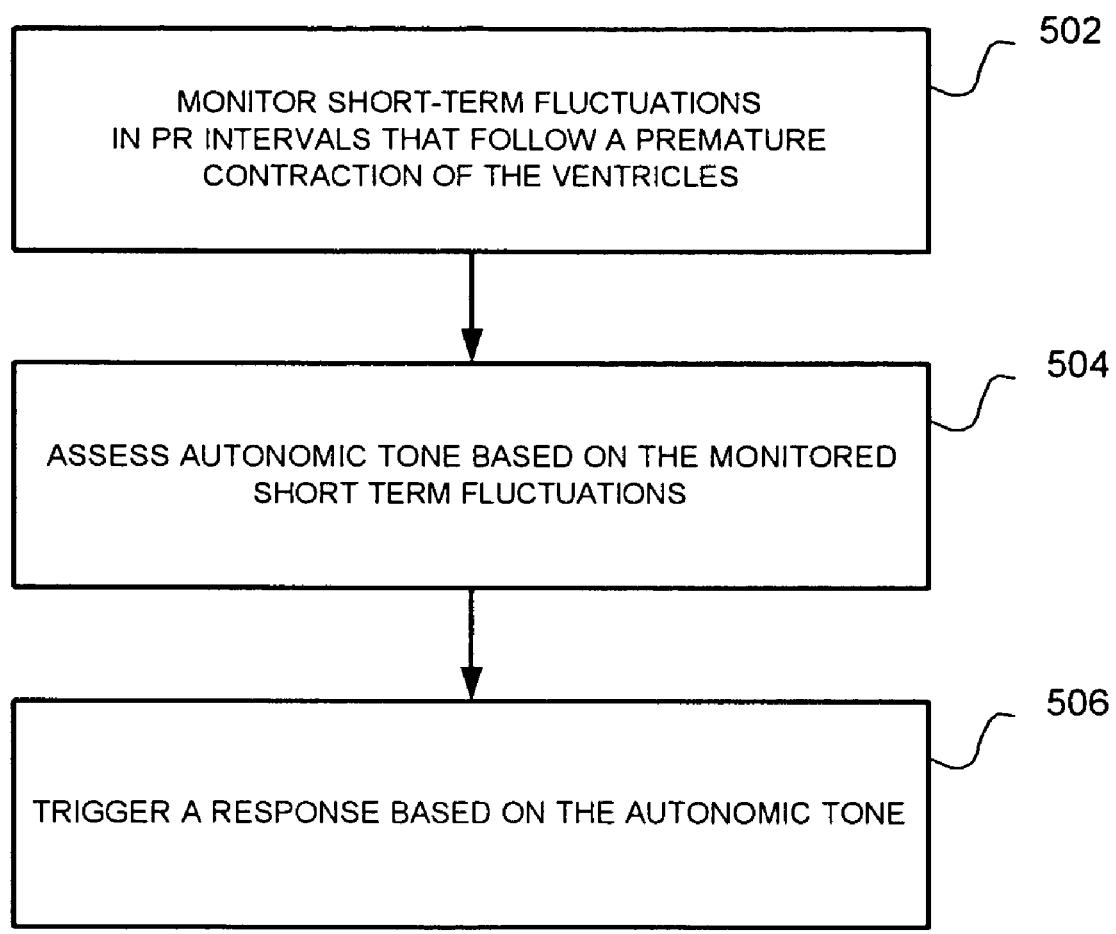
FIG. 5 is a high-level flow diagram that is useful for describing embodiments of the present invention that relate to assessing a patient's autonomic tone, which is useful e.g., for monitoring disease progression.

As shown in FIG. 5, at step 502 short-term fluctuations in PR intervals that follow a premature contraction of the ventricles are monitored. Since this step is virtually identical to step 402 described above with reference to FIG. 4, it need not be described again in detail. At step 504, autonomic tone is assessed based on the monitored fluctuations, and at step 506 one or more response can be triggered in response to the autonomic tone assessment.

At step 504, a reduction in fluctuations in PR intervals are recognized as being indicative of a reduction in parasympathetic tone, and/or an increase in sympathetic tone. Conversely, an increase in fluctuations in PR intervals is recognized as being indicative of an increase in parasympathetic tone, and/or a decrease in sympathetic tone.

At step 506, one or more response can be triggered based on the assessed autonomic tone. In accordance with an embodiment of the present invention, information related to autonomic tone can be stored for later retrieval and/or transmission to a physician or other clinician. This can include, for example, storing the PR intervals, a degree of fluctuations in the PR intervals and/or a degree of autonomic tone. Such information can basically be displayed with previously determined autonomic tone information, from say a month ago, and compared to see improvement or worsening of a disease state, e.g., heart failure. Such information can be continually, or from time to time, automatically uploaded to an external device (e.g., 102), in similar manners as were described above with reference to step 406. In certain embodiments, a patient is alerted when, e.g., a reduction in parasympathetic tone, or an increase in sympathetic tone, is sufficiently high to warrant an alert, thereby allowing the patient to respond appropriately. More details of such alerts were described above with reference to step 406, and thus need not be described in detail again.

Step 502 and 504 can be repeated from time to time so that changes in a patients autonomic tone can be monitored. It is also within the scope of the present invention that step 502 is repeated multiple times (e.g., 20 times) before a patient's autonomic tone is assessed at step 504. For example, a separate level or degree of autonomic tone can be assessed following each of a plurality of premature contractions of the ventricles, and then a combined degree/level of autonomic tone can be determined. Alternatively, PR interval data associated with a plurality of premature contractions of the ventricles can be ensemble averaged, and autonomic tone can be assessed based on the ensemble averages. It is also possible to monitor the overall morphology of the oscillations of PR intervals following a premature contraction of the ventricles, and comparing a monitored morphology to a threshold morphology/or previously determined morphologies to monitor a patient's autonomic tone. These are just a few examples of how fluctuations in PR intervals that follow premature contraction of the ventricles can be monitored to assess a patient's autonomic tone. Based on the description herein, those of ordinary skill in the art will appreciate that other ways are also within the spirit and scope of the present invention.

Detecting Episodes of Ischemia

Depression of baroreflex sensitivity (BRS) in the acute phase as well as the chronic phase of myocardial infarction (MI) has been shown, though the mechanism is not well understood. This impairment in BRS leads to a lack of appropriate baroreflex activity in response to a hypotensive stimulus, such as premature ventricular contraction, as demonstrated by a blunted HRT, a surrogate marker for BRS. ("Reflex Cardiac Activity in Ischemia and Reperfusion: Heart Rate Turbulence in Patients Undergoing Direct Percutaneous Coronary Intervention for Acute Myocardial Infarction." Bonnemeier et al, *Circulation*, Vol. 108: Pages 958-964 (2003)). Furthermore, in the acute phase of an MI, this impairment is shown to be restored within minutes after successful reperfusion by percutaneous coronary intervention (PCI).

An inventor of the present invention has realized that the same temporary impairment of baroreflex sensitivity (BRS), which occurs during an acute or chronic phase of MI, also occurs during ischemic episodes that are followed by reperfusion. The inventor has further realized that this kind of temporary BRS deficiency makes monitoring short-term fluctuations in sinus cycle length (and other cardiac intervals, such as PR intervals) that follow premature contraction of the ventricles a good tool for monitoring myocardial ischemia. Such a technique is explained in the flow diagram of FIG. 6, and is discussed in more detail below.

Figure 6:
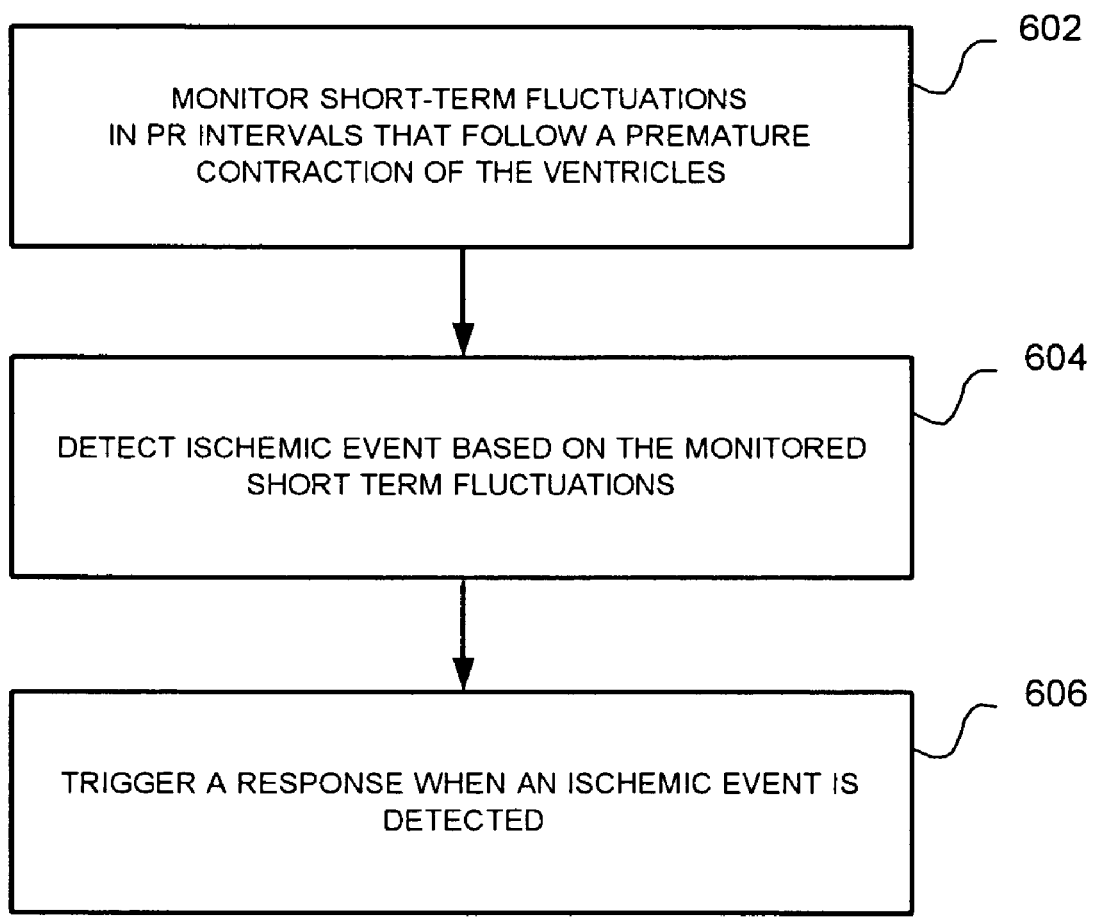
FIG. 6 is a high-level flow diagram that is useful for describing embodiments of the present invention that relate to detecting episodes of myocardial ischemia.

As shown in FIG. 6, at steps 602 short-term fluctuations in PR intervals are monitored. Since this step is virtually identical to step 402 described above with reference to FIG. 4, it need not be described again in detail. At step 604, an ischemic event is detected based on the monitored fluctuations, and at step 606 one or more response can be triggered in response to detection of an ischemic event.

Referring back to FIGS. 3B and 3C, these graphs, as explained above, are of RR intervals (vertical axis) versus successive cardiac beats (horizontal axis) which are useful for determining the short-term fluctuation in RR intervals following a premature contraction of the ventricles. In addition to being useful for explaining how risk of SCD and autonomic tone can be assessed, these graphs can also be used to describe how episodes of myocardial ischemia can be detected. More specifically, the graph of FIG. 3B can be used to illustrate the resulting short-term fluctuation in sinus cycle lengths (i.e., RR intervals) following a premature contraction of the ventricles (e.g., as shown at 306) when a patient is not experiencing an episode of myocardial ischemia. In contrast, the resulting fluctuation in cardiac intervals (RR intervals, in this example) following a premature contraction of the ventricles when the patient is experiencing an episode of myocardial ischemia, can be illustrated by the graph of FIG. 3C. As mentioned above, it is believed that the blunting of short-term fluctuations in cardiac intervals that follow a premature contraction of the ventricles is primarily a vagally mediated phenomenon. Since the vagal nerve feeds the SA node as well as the AV node, in addition to affecting RR intervals, it is believed that PR intervals that follow the premature contraction of the ventricles will also be affected. Accordingly, ischemic events can be detected based on the monitored fluctuations of PR intervals.

In accordance with certain embodiments, step 602 includes quantifying the short-term fluctuations, and more specifically quantifying a degree of the short-term fluctuations in PR intervals that follow a premature contraction of the ventricles. In accordance with an embodiment, step 604 includes identifying periods, when the measured degree crosses a corresponding threshold (in a direction indicative of diminished short term fluctuations), as myocardial ischemic events. Such thresholding may work with many patients. However, for patients that have reduced fluctuations to begin with (e.g., because they have a relative low parasympathetic tone), this type of thresholding may result in a high percentage of false positives. Accordingly, to reduce false positives, a baseline can be determined, such that a myocardial ischemic event is identified during a period (at step 604) when the measured degree of short-term fluctuations in PR intervals deviates from the baseline by more than a threshold. As will be appreciated from the following discussion, more than one baseline and threshold may be used.

It is believed that fluctuations in PR intervals may be attenuated (i.e., blunted) at higher heart rates. Accordingly, in preferred embodiments of the present invention, values of the degree of short-term fluctuations in PR intervals, that are used to determine one or more baseline, are measured (and likely stored) while a patient is at rest. A determination of whether the patient is sufficiently at rest (such that baseline measurements can be made) can be based, e.g., on heart rate measurements, on information obtained from an activity sensor (e.g., 116), or the like.

One approach for determining one or more baseline is to perform each baseline measurement after a naturally occurring (i.e., intrinsic) premature contraction of the ventricles caused by a naturally occurring VPB. A disadvantage of this technique, however, is that it cannot be executed on-demand or at regular intervals.

Another approach for determining one or more baseline, when naturally occurring premature contraction of the ventricles are absent, is to perform baseline measurements following artificially induced premature contractions of the ventricles, accomplished by prematurely stimulating the patient's right or left ventricle. This approach is discussed in U.S. patent application Ser. No. 10/861,747, which was incorporated herein by reference above. A potential disadvantage of this technique, however, is that artificially inducing premature contraction of the ventricles in this manner may be arrhythmiagenic.

A further approach for determining one or more baseline is to perform baseline measurements following an artificial stimulation of a patient's vagus nerve in order to induce a drop in arterial blood pressure, which simulates the patient's cardiovascular response to a premature contraction of the ventricles. An advantage of this technique is that it can be executed on-demand and at regular intervals, and it not likely to cause an arrhythmia. In such an approach, the patient's vagus nerve is stimulated for a duration that simulates compensatory pause 312, shown in FIG. 3B, in order to trigger an intrinsic baroreflex response to a drop in blood pressure. This is described in detail in U.S. patent application Ser. No. 10/861,747, which was incorporated by reference above, and has been discussed above. This technique is referred to herein as simulating a premature contraction of the ventricles.

Still another approach for determining one or more baseline parameter is to measure such parameter(s) following an artificially induced premature atrial contraction (PAC). An advantage of this technique is that it can be executed on-demand and at regular intervals, and is not likely to cause an arrhythmia. In such an approach, the patient's right or left atrium is stimulated prematurely to artificially induce a PAC. The PAC will be conducted through the AV node into the ventricles, thereby causing the ventricles to prematurely contract.

Baseline measurements can be averaged to produce a baseline. However, one of ordinary skill in the art would understand that more complex algorithms can be used to calculate baselines, and thus, the present invention should not be limited to averaging. Also, any averaging (or other algorithm) that is used may or may not be performed using ensemble methods (e.g., ensemble averaging). Further, a baseline is preferably updated from time to time (e.g., once a week, or once a month). Such updating can be in response to a certain amount of time passing since a last update, or in response to another specific event or events being detected.

In specific embodiments, step 602 includes measuring one or more degree of heart rate turbulence (HRT), but substituting measures of PR intervals for measures of RR intervals that are typically used to measure degrees of HRT, and step 604 includes identifying ischemic events based on the measured degree of HRT. In such embodiments, step 604 preferably includes detecting ischemic events when the degree of HRT exceeds a baseline by more than a threshold amount. Alternatively, a myocardial ischemic event can be detected at step 604 when the degree of HRT simply crosses a corresponding threshold in a direction indicative of a diminished degree of HRT (i.e., without using a baseline). The HRT parameter(s) measured at step 602 can include, e.g., turbulence morphology, turbulence onset (TO), turbulence slope (TS) and/or turbulence timing (TT).

In accordance with specific embodiments of the present invention, when determining a degree of HRT, PR intervals for an M beat sequence for each of N premature contractions of the ventricles are stored, with each premature beat being the $n^{th}$ beat within the M beat sequence. After storing the PR intervals for N of such sequences, ensemble averaging of the N sequences (of M beats each) is performed, with the premature contractions of the ventricles lined up in the same location for each sequence. Then, one or more HRT parameter (e.g., TO, TS and/or TT) is calculated based on these ensemble averages.

As has been explained above, if a person has a relatively low parasympathetic tone (which is indicative of a high risk of SCD), then they will a low degree of fluctuations in PR intervals that follow a premature contraction of the ventricles, as has be explained above with reference to FIGS. 3B and 3C. However, it is believed that a degree of fluctuation in PR intervals will be further blunted if such a patient is also experiencing an episode of myocardial ischemia. Accordingly, by determining a baseline (as described above), and detecting myocardial ischemic events when the measured degree of short-term fluctuations in PR intervals deviates from the baseline by more than a threshold, ischemic events can be detected even in those patients that normally have a relatively low degree of fluctuation in PR intervals following premature contractions of the ventricles.

Additionally, or alternatively, other techniques for detecting ischemic events can be used together with techniques described herein which related to monitoring short term fluctuations in PR intervals that follow premature contraction of the ventricles. For example, the above described embodiments can be used to supplement (e.g., to increase the confidence level of) the detection of an ischemic event using some other technique. Alternatively, some other technique can be used to supplement the detection of an ischemic event that was detected using one of the above described embodiments of the present invention. For a more specific example, in U.S. Pat. No. 6,609,023 (Fishell et al.), which is incorporated herein by reference, ST segments are analyzed for the purpose of detecting myocardial infarctions and/or myocardial ischemia. More specifically, the '023 patent discloses that ischemia can be detected by comparing ST segment shifts to an appropriate threshold, where an "ST shift" is the difference between the ST deviation of any single beat in a recently collected electrogram segment and a baseline average ST deviation extracted from a baseline electrogram segment. This is just one example of a technique that can be used together with the embodiments of the present invention that detect ischemic events based on monitored short-term fluctuations in PR intervals that follow premature contractions of the ventricles. Other techniques can be used for supplementing embodiments of the present invention. Similarly, embodiments of the present invention can be used to supplement other techniques.

Since each HRT parameter (i.e., TS, TO and TT) is expressed in different units, if more than one HRT parameter is being monitored, then a degree of HRT can be calculated using an algorithm that appropriately weights the different types of parameters to produce a single value. An appropriate baseline and threshold can be determined in a similar manner. Alternatively, a multi-dimensional table (e.g., a truth table) can be used such that each different type of parameter has its own corresponding threshold, and preferably also its own corresponding baseline. The detection of a myocardial ischemic event can then be defined as desired. For example, it may be that a myocardial ischemic event is only identified when every measured HRT parameter crosses its corresponding threshold in a direction indicative of a diminished HRT (or exceeds its baseline by more than a corresponding threshold). For another example, it may be that a myocardial ischemic event is identified when at least one HRT parameter crosses its corresponding threshold in a direction indicative of a diminished HRT (or exceeds its baseline by more than a corresponding threshold).

In a manner similar to that described above, the baselines and/dr thresholds stored in this table can be updated from time to time. Such combining of baseline measurements having different units, and/or the use of multi-dimensional tables also applies where the short-term fluctuations of other types of cardiac intervals (instead or in addition to RR interval) are being monitored.

It is also possible to monitor the overall morphology of the oscillations of PR intervals following a premature contraction of the ventricles. This can include comparing a monitored morphology to a threshold morphology, and detecting a myocardial ischemic event based on the comparison. This can also include comparing a monitored morphology to a baseline morphology, and detecting myocardial ischemic events when the monitored morphology differs from the baseline morphology by more than specified degree. A degree of similarity/difference between a monitored morphology and a baseline morphology can be accomplished, e.g., by determining a correlation between the two morphologies. Of course other techniques are also possible. As would be apparent from the above discussion, a baseline morphology is preferably based on measurements of cardiac intervals that correspond to premature contractions of the ventricles that occur while a patient is at rest.

As mentioned above, at step 606 one or more response can be triggered if a myocardial ischemic event is detected. In accordance with an embodiment of the present invention, information related to each ischemic event can be stored. This can include, for example, storing timing and duration information for each ischemic event and providing a measure of ischemia burden (which can basically be displayed with previously determined ischemia burdens from say month ago and compared to see improvement or worsening of cardiovascular condition). Such information can be continually, or from time to time, automatically uploaded to an external device (e.g., 102). Such an external monitoring device can be located, e.g., in the patients' home, and the information can be transmitted (e.g., through telephone lines or the Internet) to a medical facility where a physician can analyze the information. Alternatively, the external device can be located at a medical facility, and the information can be uploaded when the patient visits the facility. In accordance with an embodiment of the present invention, the duration information for each ischemic event is indicative of the time from when sufficiently blunted short term fluctuations in PR intervals (following a premature contraction of the ventricles) are first detected to the time that such fluctuations are sufficiently restored. This can be accomplished, e.g., by repeatedly reassessing a degree of fluctuations after sufficiently blunted fluctuations (as defined by one or more threshold) are first detected. Then, when sufficiently restored fluctuations (as defined by one or more threshold) are detected, it can be assumed that the period of ischemia has ended. Adding ST segment analysis to this can further increase duration specificity.

A myocardial infarction (i.e., a heart attack) is always preceded by a myocardial ischemic event. Thus, the detection of a myocardial ischemic event may be indicative of an immanent myocardial infarction. Accordingly, in an embodiment, a patient is alerted when a myocardial ischemic event is detected, thereby allowing the patient to respond appropriately. Such an alert could be a vibratory or auditory alert that originates from within an implantable device. Alternatively, an implantable device may wirelessly transmit an alert to an external device that produces a visual or auditory alert that a patient can see or hear. The alert may inform that patient that he should rest, or if the patient is operating some type of dangerous machinery (e.g., a car), that the patient should stop what they are doing. By alerting the patient to rest, a myocardial infarction may be avoided, or if it does occur, the patient will be less dangerous to themselves and others if the patient is resting when the infarction occurs (as opposed, e.g., to driving a car).

Additionally or alternatively, the patient can be instructed to take medication when alerted. In still another embodiment, a physician or other person (e.g., a caregiver, guardian or relative of the patient) is alerted whenever a myocardial ischemic event is detected.

In further embodiments, a myocardial ischemia therapy can be triggered in response to detecting an ischemic event. One type of therapy would be for an implanted device (e.g., device 10) to stimulate the vagal nerve, in an attempt to slow down the heart rate. In another embodiment, the implanted device, if appropriately equipped, can deliver an appropriate drug therapy. One of ordinary skill in the art would appreciate from the above description that other types of therapies can be triggered.

These are just a few examples of the types of responses that can be performed upon detection of a myocardial ischemic event. One of ordinary skill in the art would understand from the above description that other responses are also possible, while still being within the spirit and scope of the present invention.

As mentioned above, fluctuations in cardiac intervals may be normally attenuated (i.e., blunted) at higher heart rates. Accordingly, it may be beneficial to also monitor heart rate and or activity (using a single or multi-dimensional activity sensor) and to store such information together with timing and duration information for each detected ischemic event.

Figure 7:
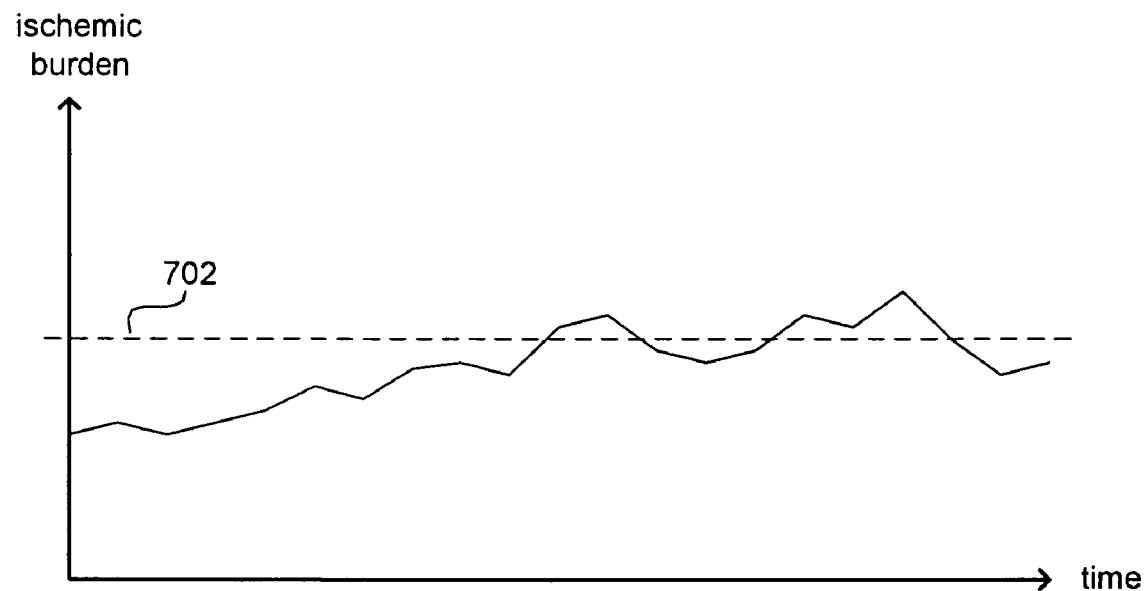
FIG. 7 is an exemplary graph of myocardial ischemic burden versus time that can be produced using embodiments of the present invention.

In accordance with an embodiment of the present invention, ischemic burden can be monitored by determining a number of ischemic events that occur during each predetermined period of time (e.g., 24 hours). By tracking ischemic burden in this manner, there can be a determination of whether ischemic burden has increased or decreased over time. Additionally, one or more ischemic burden threshold can be defined, so that one of the above responses can be triggered in response to a specific ischemic burden threshold being crossed. FIG. 7 shows an exemplary graph of ischemic burden over time, with dashed line 702 representing an exemplary threshold.

Figure 8:
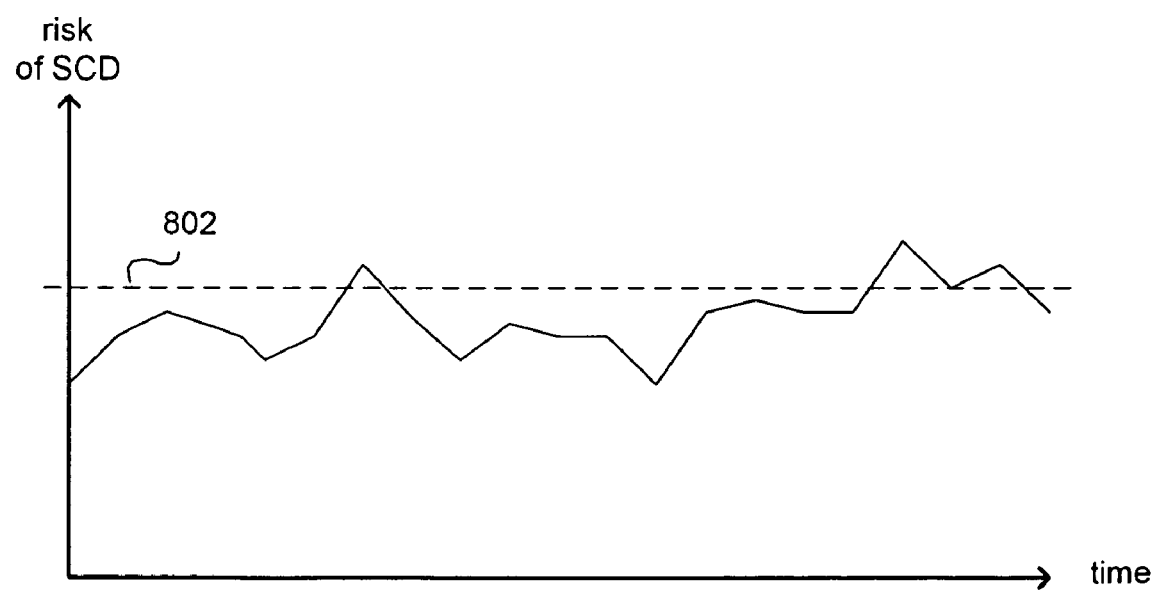
FIG. 8 is an exemplary graph of risk of SCD versus time that can be produced using embodiments of the present invention.

It is also possible to simultaneously monitor both myocardial ischemia and risk of SCD. For example, a risk of SCD over time can be monitored, e.g., as shown in FIG. 8, while ischemic burden is monitored over the same period of time, e.g., as shown in FIG. 7. Different responses can then be triggered based on both risk of SCD and ischemic burden. For example, a first response can be triggered when risk of SCD crosses its threshold, while the ischemic burden is below its threshold (e.g., represented by dashed line 802); a second response can be triggered if risk of SCD does not cross its threshold, but ischemic burden crosses its threshold; and a third response can be triggered when both risk of SCD and ischemic burden each cross their corresponding thresholds. Also, as explained above, there can be more than one threshold for each type of assessment being monitored, thereby enabling more than three different responses to potentially be triggered.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein.

Thus, the breadth and scope of the present invention should not be limited by any of the above-described exemplary embodiments, but should be defined only in accordance with the following claims and their equivalents.

What is claimed is:

1. For use with an implantable system, a method of performing at least one of a cardiac assessment and an autonomic assessment, comprising:
   (a) monitoring short-term fluctuations in PR intervals that follow a premature ventricular contraction; and
   (b) performing, using a processor of the implantable system, at least one of a cardiac assessment and an autonomic assessment, based on the monitored fluctuations in PR intervals that follow the premature ventricular contraction.

2. The method of claim 1, wherein step (b) comprises assessing a patient's risk of sudden cardiac death (SCD) based on the monitored fluctuations in PR intervals that follow the premature ventricular contraction.

3. The method of claim 1, wherein step (b) comprises assessing a patient's autonomic tone based on the monitored fluctuations in PR intervals that follow the premature ventricular contraction.

4. The method of claim 3, wherein step (b) includes at least one of the following:
   recognizing a reduction in fluctuations in PR intervals as being indicative of a reduction in parasympathetic tone;
   recognizing a reduction in fluctuations in PR intervals as being indicative of an increase in sympathetic tone;
   recognizing an increase in fluctuations in PR intervals as being indicative of an increase in parasympathetic tone; and
   recognizing an increase in fluctuations in PR intervals as being indicative of a decrease in sympathetic tone.

5. The method of claim 1, wherein step (b) comprises detecting a myocardial ischemic event based on the monitored fluctuations in PR intervals that follow the premature ventricular contraction.

6. The method of claim 5, wherein step (b) comprises detecting a myocardial ischemic event by detecting a temporary blunting of the monitored fluctuations in PR intervals that follow the premature ventricular contraction.

7. The method of claim 1, wherein step (b) comprises assessing a patient's risk of sudden cardiac death (SCD) based on the monitored fluctuations in PR intervals that follow the premature ventricular contraction; and further comprising alerting at least one of a patient and a medical practitioner in response to assessing a high risk of SCD.

8. The method of claim 1, wherein step (b) comprises assessing a patient's risk of sudden cardiac death (SCD) based on the monitored fluctuations in PR intervals that follow the premature ventricular contraction; and further comprising triggering cardiac therapy in response to assessing a high risk of SCD.

9. The method of claim 1, wherein the premature ventricular contraction can be intrinsic, induced or simulated.

10. The method of claim 1, wherein step (a) includes monitoring PR intervals that both precede and follow the premature ventricular contraction, such that PR intervals that precede the premature ventricular contraction can be used in calculating the short-term fluctuations in PR intervals that follow the premature ventricular contraction.

11. The method of claim 1, wherein step (a) includes monitoring short-term fluctuations in PR intervals within beats that follow the premature ventricular contraction.

12. For use with an implantable system, a method of performing at least one of a cardiac assessment and an autonomic assessment, comprising:
   (a) monitoring short-term fluctuations in PR intervals the follow each of a plurality of premature ventricular contractions; and
   (b) performing, using a processor of the implantable system, the at least one of a cardiac assessment and an autonomic assessment based on the monitored short-term fluctuations in PR intervals the follow the premature ventricular contractions.

13. The method of claim 12, wherein the premature ventricular contractions can be intrinsic, induced or simulated, or combinations thereof.

14. The method of claim 12, wherein a separate assessment is performed at step (b) for each of the premature ventricular contractions.

15. The method of claim 12, wherein a single assessment is performed at step (b) for multiple premature ventricular contractions.

16. The method of claim 12, wherein:
   step (a) includes determining a degree of the short-term fluctuations in PR intervals that follow each of the premature ventricular contractions; and
   step (b) includes identifying periods, when the determined degree crosses a corresponding threshold in a specified direction, as myocardial ischemic events.

17. The method of claim 16, further comprising:
   (c) assessing a patient's ischemic burden based on a myocardial ischemic event detected at step (b).

18. The method of claim 12, wherein:
   step (a) includes determining a degree of the short-term fluctuations in PR intervals that follow each of the premature ventricular contractions; and
   step (b) includes identifying periods, when the determined degree deviates from a baseline by more than a threshold, as periods of myocardial ischemic events.

19. The method of claim 18, further comprising:
   (c) assessing a patient's ischemic burden based on myocardial ischemic events detected at step (b).

20. The method of claim 12, wherein step (b) comprises assessing a patient's risk of sudden cardiac death (SCD) based on the monitored fluctuations in PR intervals that follow the premature ventricular contractions.

21. The method of claim 20, further comprising:
   (c) comparing a recently determined risk of SCD to a previously determined risk of SCD to determine whether there has been an increase or a decrease in risk of SCD.

22. The method of claim 20, further comprising:
   (c) comparing a recently determined risk of SCD to a previously determined risk of SCD to determine whether there is an imminent risk of an arrhythmia.

23. The method of claim 12, wherein step (b) comprises assessing a patient's autonomic tone based on the monitored fluctuations in PR intervals that follow the premature ventricular contractions.

24. An implantable system for performing at least one of a cardiac assessment and an autonomic assessment, comprising:
   means for monitoring short-term fluctuations in PR intervals that follow premature ventricular contractions; and
   means for performing at least one of a cardiac assessment and an autonomic assessment, based on the monitored fluctuations in PR intervals.

25. The system of claim 24, wherein the means for performing assesses a patient's risk of sudden cardiac death (SCD) based on the monitored fluctuations in PR intervals.

26. The system of claim 24, wherein the means for performing assesses a patient's autonomic tone based on the monitored fluctuations in PR intervals.

27. The system of claim 24, wherein the means for performing detects myocardial ischemic events based on the monitored fluctuations in PR intervals.

28. The system of claim 24, wherein the means for monitoring monitors PR intervals that both precede and follow each premature ventricular contraction, such that PR intervals that precede the premature ventricular contraction can be used in calculating the short-term fluctuations in PR intervals that follow the premature ventricular contraction.

* * * * *